US00PP32648P2

(12) United States Plant Patent
Barnes

(10) Patent No.: US PP32,648 P2
(45) Date of Patent: Dec. 15, 2020

(54) ***CALIBRACHOA* PLANT NAMED 'BBCAL99001'**

(50) Latin Name: *Calibrachoa*
Varietal Denomination: BBCAL99001

(71) Applicant: Brent D. Barnes, Riverside, CA (US)

(72) Inventor: Brent D. Barnes, Riverside, CA (US)

(73) Assignee: PLANT ZI LLC, Bonsall, CA (US)

( * ) Notice: Subject to any disclaimer, the term of this patent is extended or adjusted under 35 U.S.C. 154(b) by 0 days.

(21) Appl. No.: 16/873,356

(22) Filed: Mar. 26, 2020

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821
See application file for complete search history.

*Primary Examiner* — Anne Marie Grunberg
(74) *Attorney, Agent, or Firm* — C. A. Whealy

(57) ABSTRACT

A new and distinct *Calibrachoa* plant named 'BBCAL99001', characterized by its compact, upright to outwardly spreading and mounding to eventually trailing plant habit; moderately vigorous growth habit; freely branching habit; dense and bushy appearance; early and freely flowering habit; rose pink-colored flowers with bright yellow-colored star-shaped central pattern; and good garden performance.

2 Drawing Sheets

Figure 1:
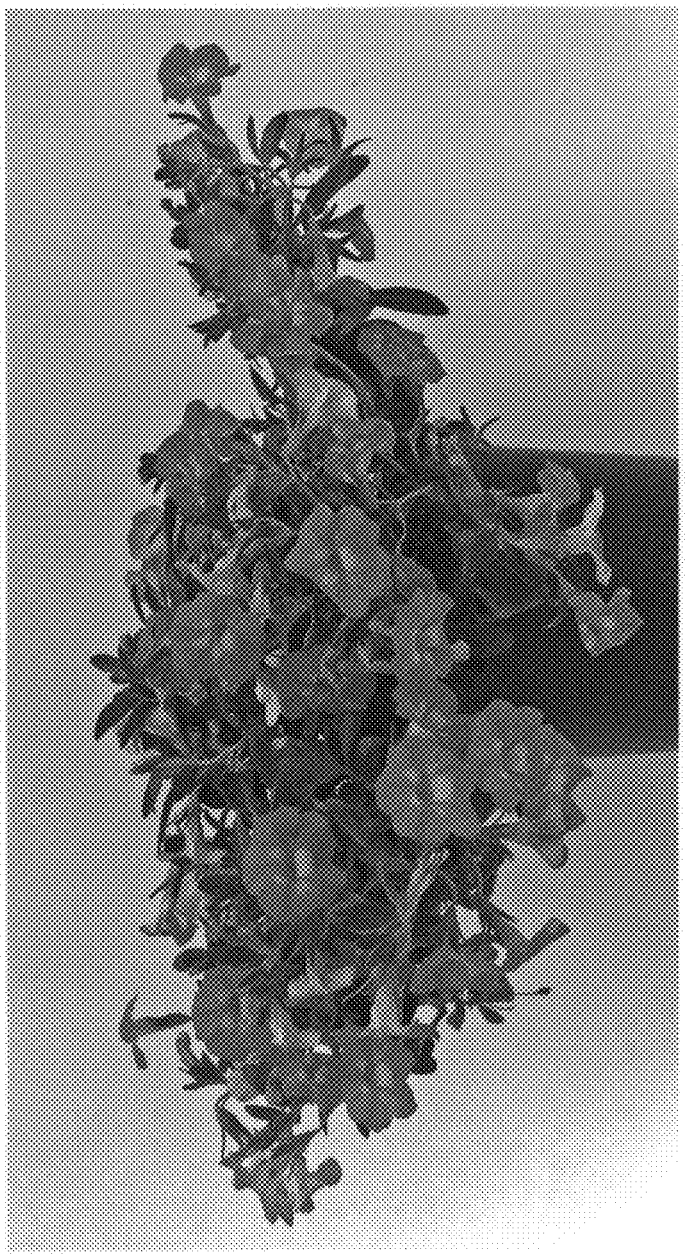

Botanical designation: *Calibrachoa* sp.
Cultivar denomination: 'BBCAL99001'.

BACKGROUND OF THE INVENTION

The present invention relates to a new and distinct cultivar of *Calibrachoa* plant, botanically known as *Calibrachoa* sp. and hereinafter referred to by the name 'BBCAL99001'.

The new *Calibrachoa* plant is a product of a planned breeding program conducted by the Inventor in Bonsall, Calif. The objective of the breeding program is to create new uniform and freely-branching *Calibrachoa* plants with unique and attractive flower colors and patterns and good garden performance.

The new *Calibrachoa* plant originated from a cross-pollination conducted by the Inventor in Bonsall, Calif. on Sep. 25, 2017 of a proprietary seedling selection of *Calibrachoa* sp. identified as code number 17CB192-01, not patented, as the female, or seed, parent with a proprietary seedling selection of *Calibrachoa* sp. identified as code number 17CB203-01, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jun. 15, 2018.

Asexual reproduction of the new *Calibrachoa* plant by vegetative terminal cuttings in a controlled greenhouse environment in Bonsall, Calif. since Jun. 19, 2018 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBCAL99001'. These characteristics in combination distinguish 'BBCAL99001' as a new and distinct *Calibrachoa* plant:

1. Compact, upright to outwardly spreading and mounding to eventually trailing plant habit.
2. Moderately vigorous growth habit.
3. Freely branching habit; dense and bushy appearance.
4. Early and freely flowering habit.
5. Rose pink-colored flowers with bright yellow-colored star-shaped central pattern.
6. Good garden performance.

Plants of the new *Calibrachoa* differ primarily from plants of the female parent selection in the following characteristics:

1. Plants of the new *Calibrachoa* are more outwardly spreading than and not as upright as plants of the female parent selection.
2. Plants of the new *Calibrachoa* and the female parent selection differ in flower color as flowers of plants of the new *Calibrachoa* are rose pink in color with bright yellow-colored star-shaped central pattern whereas flowers of plants of the female parent selection are red in color.
3. Plants of the new *Calibrachoa* have good garden performance whereas plants of the female parent selection have poor garden performance.

Plants of the new *Calibrachoa* differ primarily from plants of the male parent selection in the following characteristics:

1. Plants of the new *Calibrachoa* are more outwardly spreading than and not as upright as plants of the male parent selection.

2. Plants of the new *Calibrachoa* and the male parent selection differ in flower color as flowers of plants of the new *Calibrachoa* are rose pink in color with bright yellow-colored star-shaped central pattern whereas flowers of plants of the male parent selection are orange in color with yellow-colored centers.

Plants of the new *Calibrachoa* can be compared to plants of the *Calibrachoa* sp. 'USCALI11', disclosed in U.S. Plant Pat. No. 14,968. In side-by-side comparisons, plants of the new *Calibrachoa* differ primarily from plants of 'USCALI11' in the following characteristics:

1. Plants of the new *Calibrachoa* are more outwardly spreading than and not as upright as plants of 'USCALI11'.
2. Plants of the new *Calibrachoa* and 'USCALI11' differ in flower color as flowers of plants of the new *Calibrachoa* are rose pink in color with bright yellow-colored star-shaped central pattern whereas flowers of plants of 'USCALI11' are light red purple in color.

Plants of the new *Calibrachoa* can also be compared to plants of the *Calibrachoa* sp. 'USCALI51', disclosed in U.S. Plant Pat. No. 14,874. In side-by-side comparisons, plants of the new *Calibrachoa* differ primarily from plants of 'USCALI51' in the following characteristics:

1. Plants of the new *Calibrachoa* are more outwardly spreading than and not as upright as plants of 'USCALI51'.
2. Plants of the new *Calibrachoa* and 'USCALI51' differ in flower color as flowers of plants of the new *Calibrachoa* are rose pink in color with bright yellow-colored star-shaped central pattern whereas flowers of plants of 'USCALI11' are violet in color.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1 of 2) is a side perspective view of a typical flowering plant of 'BBCAL99001' grown in a container.

Figure 2:
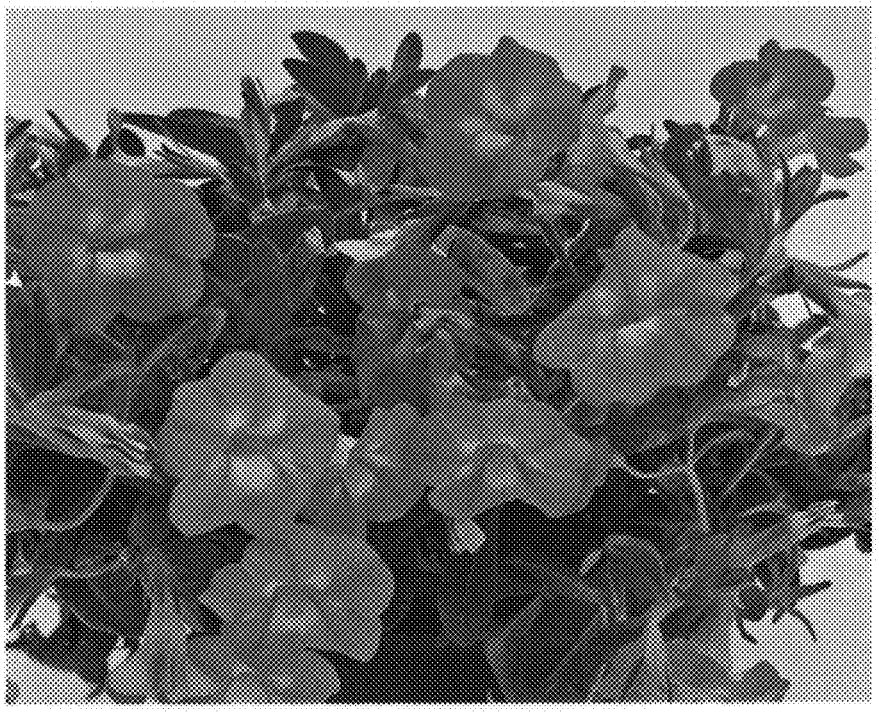

The photograph on the second sheet (FIG. 2 of 2) is a close-up view of a typical flowering plant of 'BBCAL99001'.

DETAILED BOTANICAL DESCRIPTION

The aforementioned photographs and following observations and measurements describe plants grown during the autumn and winter in 10.8-cm containers in a glass-covered greenhouse in Loudon N.H. and under cultural practices typical of commercial *Calibrachoa* production. During the production of the plants, day and night temperatures ranged from 19° C. to 21° C. Plants were pinched three weeks after planting and were 15 weeks from planting rooted cuttings when the photographs and description were taken. In the following description, color references are made to The Royal Horticultural Society Colour Chart, 2015 Edition, except where general terms of ordinary dictionary significance are used.

Botanical classification: *Calibrachoa* sp. 'BBCAL99001'.

Parentage:

*Female, or seed, parent.*—Proprietary seedling selection of *Calibrachoa* sp. identified as code number 17CB192-01, not patented.

*Male, or pollen, parent.*—Proprietary seedling selection of *Calibrachoa* sp. identified as code number 17C203-01, not patented.

Propagation:

*Type.*—By vegetative terminal cuttings.

*Time to initiate roots, summer.*—About five to seven days at ambient temperatures ranging from 17° C. to 29° C.

*Time to initiate roots, winter.*—About seven to ten days at ambient temperatures ranging from 17° C. to 21° C.

*Time to produce a rooted plant, summer.*—About four to five weeks at ambient temperatures ranging from 17° C. to 29° C.

*Time to produce a rooted plant, winter.*—About five to six weeks at ambient temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding to trailing plant habit; moderately vigorous growth habit; moderate growth rate; freely branching habit with about four to five primary lateral branches and secondary branches potentially developing at every node; dense and bushy appearance.

*Plant height, soil level to top of foliar plane.*—About 9 cm.

*Plant height, soil level to top of floral plane.*—About 10 cm.

*Plant diameter.*—About 30 cm by 34 cm.

Lateral branch description:

*Length.*—About 17 cm.

*Diameter.*—About 3 mm.

*Internode length.*—About 1.1 cm to 1.5 cm.

*Strength.*—Strong, flexible and sturdy.

*Aspect.*—About 45° to 80° from stem axis.

*Texture and luster.*—Minute pubescence; slightly glossy.

*Color, developing.*—Close to 144A.

*Color, developed.*—Close to 144A.

Leaf description:

*Arrangement.*—Before flowering, alternate; after flowering, opposite; leaves simple.

*Length.*—About 3.5 cm to 4 cm.

*Width.*—About 1.8 cm to 2.2 cm.

*Shape.*—Elliptical to obovate.

*Apex.*—Broadly acute to rounded.

*Base.*—Attenuate.

*Margin.*—Entire.

*Texture and luster, upper and lower surfaces.*—Sparse and minute pubescence, pubescence mostly along midvein and margins; slightly glossy.

*Venation pattern.*—Pinnate; arcuate.

*Color.*—Developing leaves, upper and lower surfaces: Close to 146A. Fully expanded leaves, upper surface: Close to 147A; venation, close to 146B. Fully expanded leaves, lower surface: Close to 147B; venation, close to 146B.

*Petioles.*—Length: About 7 mm to 9 mm. Diameter: About 1 mm by 2 mm. Strength: Moderately strong, flexible. Texture and luster, upper and lower surfaces: Minute pubescence; slightly glossy. Color, upper and lower surfaces: Close to 146B.

Flower description:

*Flower type and flowering habit.*—Single salverform flowers arising from leaf axils; freely flowering habit with typically about 135 flowers and flower buds developing per plant at one time; flowers face slightly upright to outwardly.

*Fragrance.*—None detected.

*Natural flowering season.*—Plants of the new *Calibrachoa* begin flowering about six to eight weeks after planting; plants flower continuously from the spring though the summer until frost.

*Flower longevity.*—Individual flowers last about four to five days on the plant; flowers persistent.

*Flower buds, before showing color.*—Length: About 7 mm to 9 mm. Diameter: About 2 mm. Shape: Oblong, elongate. Texture and luster: Minute pubescence; slightly glossy. Color: Close to 144A.

*Flower diameter.*—About 2.5 cm.

*Flower length* (*height*).—About 1.5 cm.

*Flower throat diameter.*—About 5 mm by 6.5 mm.

*Flower tube length.*—About 1 cm.

*Flower tube diameter at the base.*—About 1.5 mm.

*Corolla.*—Arrangement: Five fused petals opening into a flared trumpet. Petal lobe length (from throat): About 1 cm. Petal lobe width: About 1.1 cm. Petal shape: Spatulate. Petal apex: Obtuse to slightly emarginate; recurving with development. Petal margin: Entire; slightly moderately undulate. Petal texture and luster, upper surface: Smooth, glabrous, velvety; slightly glossy. Petal texture and luster, lower surface: Smooth, glabrous; slightly glossy. Throat texture and luster: Smooth, glabrous; slightly glossy. Tube texture and luster: Minute pubescence; slightly glossy. Color: Petal lobe, when opening and fully opened, upper surface: Close to 63A; towards the base, close to 12A to 12B; midvein, close to 53A to 53B; color does not change with development. Petal lobe, when opening and fully opened, lower surface: Close to 63D; midvein, close to 144A; color does not change with development. Throat: Close to 12A, yellow color fusing distally; venation, close to 12A. Tube: Close to 144A to 144B; venation, close to 144A to 144B.

*Calyx.*—Arrangement: One star-shaped calyx tube with five sepals fused towards the base and arranged in a single whorl; sepals flaring outwardly and reflexing towards the apex. Length: About 1.5 cm. Diameter: About 2.2 cm. Sepal length: About 1.5 cm. Sepal width: About 3 mm to 4 mm. Sepal shape: Linear to ligulate. Sepal apex: Acute. Sepal margin: Entire. Sepal texture and luster, upper and lower surfaces: Minute pubescence; slightly glossy. Sepal color, when developing, upper and lower surfaces: Close to 146A. Sepal color, developed, upper surface: Close to 146A. Sepal color, developed, lower surface: Close to 146B.

*Peduncles.*—Length: About 1.3 cm. Diameter: About 1.25 mm. Angle: About 45° to 55° from stem axis. Strength: Strong, wiry and flexible. Texture and luster: Minute pubescence; slightly glossy. Color: Close to 146B to 146C.

*Reproductive organs.*—Stamens: Quantity: Five per flower. Filament length: About 7 mm. Filament color: Close to 145C to 145D. Anther size: About 1 mm by 1 mm. Anther shape: Round. Anther color: Close to 8B to 8C. Pollen amount: Scarce to moderate. Pollen color: Close to 8B. Pistils: Quantity: One per flower. Pistil length: About 1.1 cm. Style length: About 8 mm. Style color: Close to 144D. Stigma diameter: About 1 mm. Stigma shape: Round. Stigma color: Close to 144A to 144B. Ovary color: Close to 144A to 144B.

*Seeds and fruits.*—To date, seed and fruit development have not been observed on plants of the new *Calibrachoa.*

Garden performance: Plants of the new *Calibrachoa* have been observed to have good garden performance and tolerate wind, rain and to be suitable for USDA Hardiness Zones 9 to 11.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'BBCAL99001' as illustrated and described.

* * * * *